United States Patent
Lehmann et al.

(10) Patent No.: US 7,767,443 B2
(45) Date of Patent: Aug. 3, 2010

(54) DEVICE AND METHOD FOR DETECTING CELLULAR PROCESSES BY MEANS OF LUMINESCENCE MEASUREMENTS

(75) Inventors: Mirko Lehmann, Freiburg (DE); Holger Klapproth, Freiburg (DE)

(73) Assignee: Micronas GmbH, Freiburg (DE)

( * ) Notice: Subject to any disclaimer, the term of this patent is extended or adjusted under 35 U.S.C. 154(b) by 1033 days.

(21) Appl. No.: 10/509,040

(22) PCT Filed: Mar. 5, 2003

(86) PCT No.: PCT/EP03/02252

§ 371 (c)(1),
(2), (4) Date: Mar. 14, 2005

(87) PCT Pub. No.: WO03/080789

PCT Pub. Date: Oct. 2, 2003

(65) Prior Publication Data

US 2005/0153387 A1    Jul. 14, 2005

(30) Foreign Application Priority Data

Mar. 27, 2002  (EP) .................................. 02006978
Jul. 26, 2002  (EP) .................................. 02016793

(51) Int. Cl.
*C12M 1/34* (2006.01)
*C12M 3/00* (2006.01)

(52) U.S. Cl. ................. 435/288.7; 435/40.5; 435/287.1; 435/287.2; 435/287.3

(58) Field of Classification Search ............. 435/288.7, 435/808, 40.5, 287.1–287.3; 422/52

See application file for complete search history.

(56) References Cited

U.S. PATENT DOCUMENTS

| 4,385,113 | A | * | 5/1983 | Frosch et al. ................... 435/8 |
| 4,621,059 | A | * | 11/1986 | Rokugawa ............... 435/287.9 |
| 5,223,402 | A | * | 6/1993 | Abbas et al. .................. 435/18 |
| 5,278,048 | A | * | 1/1994 | Parce et al. .................... 436/29 |
| 5,567,598 | A | * | 10/1996 | Stitt et al. ..................... 435/29 |

(Continued)

FOREIGN PATENT DOCUMENTS

WO    WO 99/57310    11/1999

(Continued)

OTHER PUBLICATIONS

Miller et al., "Imaging [Ca2+]$_i$ with Aequorin Using a Photo Imaging Detector," Methods in Cell Biology, vol. 40, 305-338 (1994).

(Continued)

*Primary Examiner*—Walter D Griffin
*Assistant Examiner*—Shanta G Doe
(74) *Attorney, Agent, or Firm*—O'Shea Getz P.C.

(57) ABSTRACT

A device includes a carrier element with a surface prepared for direct or indirect coupling or receiving of cells, at least one optical detector to receive a luminescence signal, the detector being integrated into the carrier element below the prepared surface, a cover covering the prepared surface to form a cavity, the cover having an inlet opening and an outlet opening, and an excitation source connected to the inlet opening. The excitation source constitutes a reservoir for a chemical or biological excitation substance or medium that influences the metabolism of the cell, with metabolic processes being made visible by luminescence and detected by at the least one optical detector.

20 Claims, 4 Drawing Sheets

U.S. PATENT DOCUMENTS

| | | | |
|---|---|---|---|
| 5,582,697 A * | 12/1996 | Ikeda et al. | 205/777.5 |
| 5,798,214 A * | 8/1998 | Squirrell | 435/7.4 |
| 6,078,705 A | 6/2000 | Neuschäfer et al. | 385/12 |
| 6,103,479 A | 8/2000 | Taylor | 435/7.2 |
| 6,104,495 A * | 8/2000 | Sieben et al. | 356/432 |
| 6,210,910 B1 | 4/2001 | Walt et al. | 435/7.32 |
| 6,469,785 B1 | 10/2002 | Duveneck et al. | 356/244 |
| 6,548,263 B1 * | 4/2003 | Kapur et al. | 506/32 |
| 6,967,086 B2 * | 11/2005 | Guarino et al. | 435/34 |
| 2002/0182631 A1 | 12/2002 | Schurmann-Mader et al. | 435/6 |

FOREIGN PATENT DOCUMENTS

| | | | |
|---|---|---|---|
| WO | WO 99/58963 | 11/1999 | |
| WO | WO 00/75644 | 12/2000 | |
| WO | WO 01/13096 | 2/2001 | |
| WO | WO/01/43875 | * 6/2001 | |
| WO | WO 03/008974 | 1/2003 | |

OTHER PUBLICATIONS

B. Streetman, "Solid State Electronic Devices," Prentice-Hall, Inc., ISBN 0-13-10 436379-5, pp. 201-227 (1995).

Iordanov et al., "Integrated High Rejection Filter for NADH Fluorescence Measurements," Sensors 2001 Proceedings, vol. 1, May 8-10, pp. 107-111, AMA Service (2001).

* cited by examiner

DEVICE AND METHOD FOR DETECTING CELLULAR PROCESSES BY MEANS OF LUMINESCENCE MEASUREMENTS

BACKGROUND OF THE INVENTION

The present invention relates to a method and a device for location-specific detection of a luminescence event or for detection of a luminescence signal in, at, or in the immediate vicinity of a cell to be analyzed.

A device according to the species for optical examination of a cell is known from EP 0 881 490 A2. This device has a substrate, particularly a semiconductor substrate, with a surface suitable for accepting cells, a number of photodetectors formed below the surface, and multiple light sources above the surface. The detectors arranged in a matrix pick up the light emitted by the light sources, which brings about various light intensities at various detectors, which are governed by a cell placed on the surface, from which information on the geometry of the cell can be obtained.

For some applications, for example in pharmaceutical research, it is particularly relevant to be able to investigate the behavior of cells in response to a chemical or biochemical stimulus. Investigating metabolic processes in living cells is particularly useful since for example the influence of a new potential drug can thereby be observed. One measurement frequently performed in this connection is intracellular calcium determination by calcium-sensitive dyes, Fura II for example. A. L. Miller, E. Karplus, L. F. Jaffe: "Coelenterate Imaging [Ca2+]$_i$ with Aequorin Using a Photon Imaging Detector," Meth Cell Bio. 40, 305 (1994) teaches the loading of cells, for example by osmotic shock treatment, with a bioluminescent substance, for example aequorin. Intracellular calcium signals as responses to chemical excitation are made visible due to the bioluminescence of aequorin.

What is needed is a compact and relatively easily realizable device and a corresponding method for detecting cellular processes by luminescence measurements using chemical or biochemical stimuli.

SUMMARY OF THE INVENTION

The device according to the invention comprises a carrier element with a surface prepared for direct or indirect coupling or receiving of cells, at least one optical detector to receive a luminescence signal, the detector being integrated into the carrier element below the prepared surface, a cover covering the prepared surface to form a cavity, the cover having an inlet opening and an outlet opening, and an excitation source connected to the inlet opening.

The excitation source constitutes a reservoir for a chemical or biological excitation substance or medium that for example influences the metabolism of the cell, with metabolic processes being made visible by luminescence and detected by the at least one optical detector.

The term "luminescence" as used below covers all light emissions brought about by and given off by a medium, and more broadly also emission of ultraviolet and infrared radiation, which emissions are caused not by high temperatures but by prior biological or chemical excitation. Substances exhibiting luminescence are known as luminophores. As is known to the individual skilled in the art, such luminescence can be elicited by chemical excitation, in which case it is termed chemoluminescence or bioluminescence. The general principles of quantum mechanics underlie this process, which causes excitation of atoms and molecules that then return to their ground state with emission of light, which is detected according to the invention.

The device according to the invention, serving for the chemical excitation of cells for detection of the emitted luminescence signals, comprises in one embodiment a wavelength filter between the prepared surface and the at least one optical detector. Preferably, a plurality of optical detectors is present, and wavelength filters with different transmission characteristics can be associated with the individual detectors for selective detection of luminescence signals with different wavelengths.

In one embodiment, the carrier element is in the form of a semiconductor body, with an evaluation circuit preferably being integrated into the semiconductor body. The use of an inorganic semiconductor material such as silicon has the advantage that traditional and previously known technology processes such as CMOS processes can be used for manufacturing the carrier with the optical detectors and the evaluation circuit.

Integration of the evaluation circuit into the semiconductor body makes it possible to preprocess the detector signals in the immediate vicinity of the cells to be analyzed. Thus, in this preferred embodiment of the device of the present invention, the device is a "smart" sensor that is capable of far more than other merely passive sensors. For example, the output signals of the electrooptical detectors can be processed by an integrated circuit so that they can be fed outward without any great difficulty via output circuits and connecting contacts. Also, preprocessing may consist of digitization of the analog signals output from the optical detectors and their conversion into an appropriate data stream. Moreover, the signal to noise ratio can be improved by the proximity of the optical detector to the signal processing location in the device according to the invention, due to the relatively short signal path. In addition, other processing steps are possible, by which for example the data volume can be reduced, or which are used for external processing and display. It is thus possible for the remaining evaluation of the optical signals and their display to be done on a personal computer (PC). Moreover, the device according to the invention can be designed such that the preferably compacted or prepared data can be transmitted by an infrared or radio connection to correspondingly equipped receiver stations.

Furthermore, there is also an option of interest from the cost point of view of using organic semiconductor materials as described for example in EP-A-1085319 for the carrier with the optical detectors.

The optical detectors, located below the prepared surface for receiving cells, are preferably in the form of photodiodes, CCD sensors, or photoconductors. Preferably, a plurality of such detectors is integrated matrix-fashion into the carrier in order to carry out a spatially resolved luminescence measurement.

In one embodiment, the excitation source, which is connected to the inlet opening of the cover, controls, through the evaluation circuit, an excitation medium at the inlet opening to which the cell immobilized at the prepared surface is exposed. For controlling the supply of medium, for example, a valve is disposed in an inlet line between the excitation source and the inlet opening, the valve being controlled by the evaluation circuit.

In order to bind the cells to the prepared surface of the carrier element, there is the option of placing at the prepared surface an adhesion matrix or a medium such as gelatin that enhances cell adherence and/or cell growth, and allowing the cells actually to grow on this nutrient medium. There is also the option of placing cells on a cell-immobilizing layer, for example negatively charged polystyrene, on the surface.

In one embodiment of the invention, a cell or a cell cluster is immobilized at the prepared surface by the manufacturer, enabling a customer to make measurements on the cell immediately after adding a selected excitation medium to the excitation source.

Preferably, the carrier element has several optical detectors or detector fields, spatially separated from each other, in order to conduct parallel measurements on several cells or cell clusters. These individual optical detectors or detector fields are preferably disposed separately such that essentially no light emission from a point or field can be picked up by the detector or detectors for another point or field. Thus, the individual detector sites can be disposed in their own depressions, as is known for example with familiar microtiter plates. Preferably, the depressions and the like according to the invention are trough-shaped such that their side walls are essentially perpendicular to the prepared surface of the device. The dimensions of such a depression may be chosen freely by the individual skilled in the art from knowledge of the application and the depression is preferably at least 100 nm deep in the prepared surface of the carrier element.

Alternatively, vertical partitions pointing upward can be disposed on the essentially planar prepared surface, with their dimensions being at the option of the individual skilled in the art based on knowledge of the application and the spatial dimensions of the cells. Suitable partitions can be applied for example by anodic bonding or by the flip-chip method. Such a device with several detector fields according to the invention makes sensor-supported electrooptical image capturing possible.

In one method according to the invention for detecting cellular processes by detection of luminescence events in, at, or in the immediate vicinity of a cell, a cell cluster, or a tissue, a device is provided having a carrier element with a surface prepared for direct or indirect coupling of cells, at least one optical detector integrated into the carrier element below the prepared surface for receiving a luminescence signal, a cover covering the prepared surface to form a cavity, the cover having an inlet opening and an outlet opening, and an excitation source connected to the inlet opening. At the surface prepared for accepting cells, at least one cell is immobilized, following which a physical or chemical excitation medium is supplied to the cavity from the excitation source, and resulting luminescence events are picked up or sensed by the at least one optical detector.

The luminescence events are preferably temporally resolved. This means that, after an excitation medium has been supplied to the environment of the cell, the light conditions at the optical detectors are evaluated at multiple sequential points in time, for example at the rate of one point per nanosecond.

In order to make metabolic events in the cell visible by luminescence, it is necessary to use luminophores that react with the metabolic products of interest by luminescing, which is picked up or sensed by the detectors.

The luminophores suitable for specific applications may be selected in a way familiar to the individual skilled in the art depending on the metabolic product to be detected, with which the luminophore is to react. Luminophores with different half-lives can be differentiated. The half-life indicates the length of time for which luminescence can be measured after excitation. The choice of a luminophore with a half-life appropriate for the particular application is a matter for judgment by the individual skilled in the art. Luminophores whose half-lives are considerably longer than 5 ns, preferably between 100 µs and 2000 µs, are particularly suitable.

The following are suitable in principle: organic luminophores, rare earth metals (lanthanides) or actinide compounds, microspheres (e.g. FluoSpheres® europium luminescent microspheres, molecular probes), or nanocrystals of semiconductors, the latter, in addition to their luminescence properties, being relatively small in size (a few nm) and highly stable (no photobleaching). Other suitable luminophores are alkaline earth halides with lattice defects, which can be made for example by doping (foreign ions) or radioactive radiation.

Most of the above-listed dyes are suitable only for measurements at or in the immediate vicinity of the cells. However, there are methods for rendering cell membranes permeable to dyes and reporter molecules. Examples of such methods are:

acetoxymethyl (AM) ester loading
acid loading (especially for plant cells)
ATP-induced permeabilization
cationic liposome delivery
electroporation
hypoosmotic shock
influx pinocytic cell-loading reagent One appropriate loading system is that described by K. Barber et al.: "Delivery of Membrane-Impermeant Fluorescent Probes into Living Neural Cell Populations by Lipotransfer," *Neurosci. Lett.* 15, 207, 17 (1996).

In one embodiment of the method, the luminescence signal detected by the optical detector or detectors is compared with a reference value. This reference value can be stored in a memory in the semiconductor body and can be obtained for example by a measurement before excitation of the cell. The reference value can also be obtained in parallel with the measurement at the cell by providing several spatially separated optical detectors or detector fields, with no cell being immobilized in the region of one detector or detector field. Thus, detected luminescence signals of this one detector or detector field are used as a reference value which takes into account light or radiation influences not caused by the cells to be analyzed, such as the natural fluorescence of system components, and can thus be deducted.

If the prepared surface of the carrier element is designed as a microarray in which a plurality of detector fields each having a number of optical detectors is present, detection of the measurement field or point signal values can be sequential by detecting whole rows or columns of the prepared surface or parts thereof one after the other (i.e., a multiplex application).

The use of multiple parallel detector fields at which the same measurements are carried out at each one also has the advantage that several measurement results are available, from which an overall measurement result can be averaged.

The output signals of the optical detectors can be evaluated in the semiconductor chip or fed by suitable circuits to an external evaluation device after analog-digital conversion.

It is clear to the individual skilled in the art that the choice of the optical detector or material depends on the emission wavelength of the dye to be detected. In principle, because of the so-called "semiconductor band gap," the optical detector has different sensitivities regarding the wavelength of the detected luminescence signal depending on which material is chosen (e.g. silicon or germanium). In the preferred case where a silicon photodiode is used, a sensitivity range from infrared to the ultraviolet wave spectrum is obtained, with the sensitivity being at its greatest between these regions (see for example B. Streetman: "Solid State Electronic Devices," Prentice-Hall, Inc., ISBN 0-13-10 436379-5, pp. 201-227 (1995).

To detect luminescences of different wavelengths, either wavelength-specific photoelements or traditional photodiodes are chosen that are equipped with mechanically applied, vapor-deposited, or integral wavelength filters. For example, it is known that silicon nitride, by contrast to silicon oxide, is impermeable to UV light and that polysilicon absorbs UV radiation (see for example V. P. Iordanov et al.: "Integrated High Rejection Filter for NADH Fluorescence Measurements," Sensors 2001 Proceedings, Vol. 1, May 8-10, pp. 106-111, AMA Service (2001)). Thus, nitride or polysilicon can be deposited on the gate oxide layer as part of the usual CMOS process, by means of which a corresponding filter is created on the photodiode. Thus, for example, NADH (nicotinamide adenine dinucleotide) has an excitation wavelength of 350 nm and an emission wavelength of 450 nm. When a filter filtering out 350 nm is applied, the sensitivity can be increased.

This effect can be utilized for differential detection when for example two different luminophores, from which for example only a light in the UV range is emitted, are used in parallel, as the detectors provided therefor are made to be UV-sensitive or not. Also, this effect provides the possibility of excluding from the measurement process any materials present that have natural fluorescence that may interfere, and that have known emission wavelengths, by providing the appropriate filters. One example of this is the parallel use of europium chelates (emission at approx. 620 nm) and copper-doped zinc sulfide (emission at approx. 525 nm) that make possible two-color detection because their emission wavelength regions are sufficiently far apart, for example within one region of a detector point or detector field, by for example providing half the sensors of a detector point or detector field with a low-pass filter and the remaining sensors of the same point or field with a high-pass filter.

Additionally or alternatively, different luminophores may be used in parallel as long as their physical or optical properties are sufficiently different. For example, according to the invention the different excitation wavelengths of two luminophores A and B to be used and/or their different half-lives are used. This can be done for example by providing two differently doped nanocrystals.

The signals of the detectors are received at an evaluation unit. The evaluation unit has a very fast converter to convert analog detector signals into digital values, which are stored. Evaluation of the digital values is preferably done in real time but can also be done on a delayed basis. An ordinary microprocessor can be used for evaluating the digital values. If the luminescence signal is too weak for definitive detection, in a preferred detection embodiment, the detection sensitivity can be heightened by integrating several individual measurements. Here, several identical measurements are carried out and the results are added together. This can be done directly on the sensor chip or after the measurement by appropriate software.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
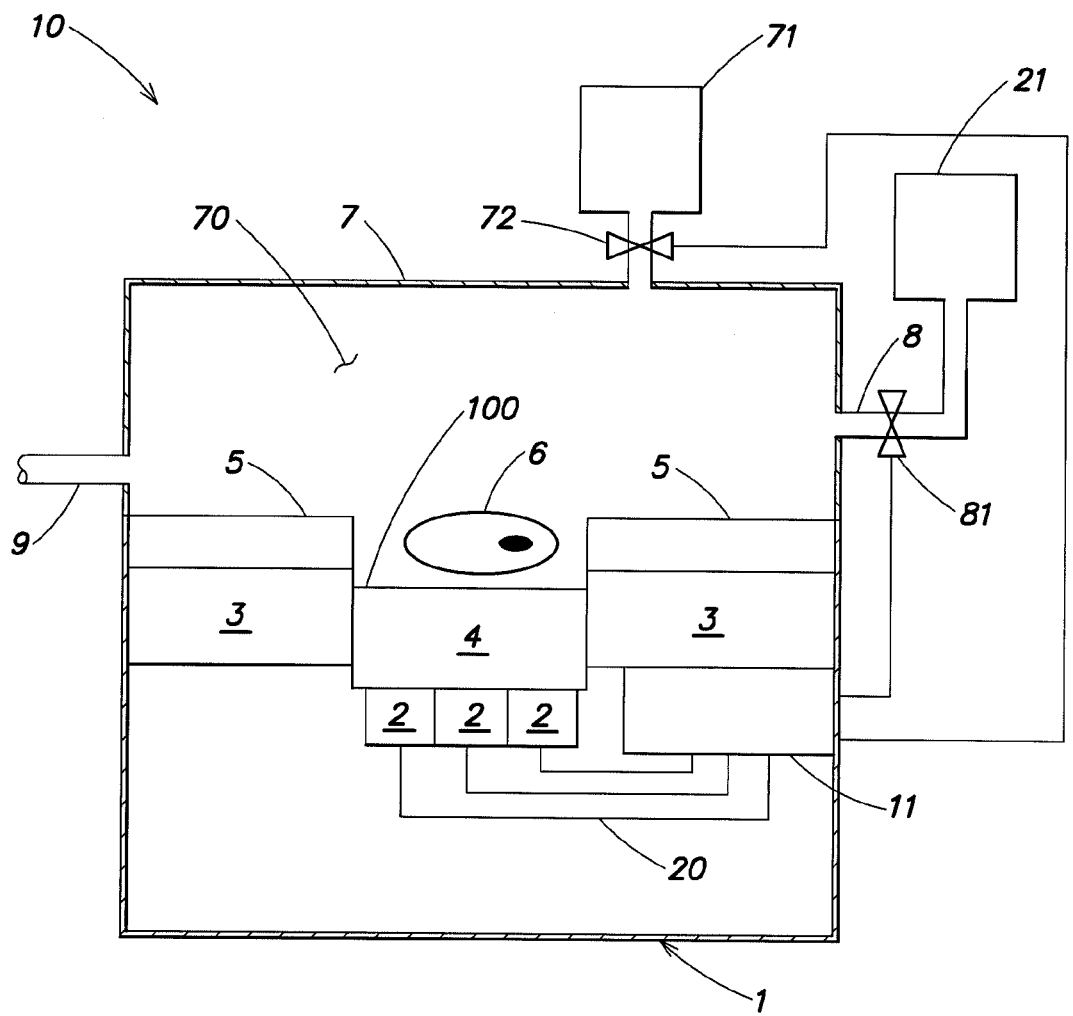
FIG. 1 is a side view in partial cross section of a first exemplary embodiment of a device according to the invention for detection of cellular processes by luminescence measurements.

FIG. 1 illustrates a first exemplary embodiment of a device 10 according to the invention for detection of a luminescence event in, at, or in the immediate vicinity of a cell, a cell cluster, or a tissue, with only one cell 6 being shown in FIG. 1 for clarity. The device 10 has a carrier element 1 with a surface 100 prepared for direct or indirect coupling or accepting of cells. For this purpose, the surface 100 includes for example a gelatin layer on which the cell has already grown, or another substance suitable for immobilizing a cell or a cell cluster. Located above the surface 100 is a cover 7 forming a cavity 70, with the cell 6 being disposed in this cavity 70. The cover 7 has an inlet 8 and an outlet 9, with the inlet 8 being connected to an excitation source 21 holding an excitation medium.

The device 10 examines the behavior of the cell 6 upon a chemical or biochemical excitation by the excitation medium contained in the excitation source 21, by means of luminescence measurements. The luminescence is created by luminophores that are introduced, in a sufficiently well-known manner, in the cell 6 or in a nutrient solution in the vicinity of the cell 6, and which react for example with a metabolic product of the cell 6. The luminescence is detected by optical detectors 2, for example photodiodes that are integrated below the surface 100 in the carrier element 1. In the example, a wavelength filter 4 is formed between the surface 100 with the cell 6 and the detectors 2. Preferably an optically transparent insulation layer not shown in detail is applied to the detectors 2 to prevent leakage currents across the surface 100, provided the filter 4 is not electrically insulating.

A scratch protector 3 with a surface coating 5, for example a precious metal or a hydrophobic/hydrophilic material, is applied to the carrier element 1, with the scratch protector 3 having a channel cut away above the detectors 2, at the bottom of which are the filter 4 and the surface 100 prepared for receiving the cell 6.

An evaluation circuit 11 (shown schematically in FIG. 1) is furthermore integrated into the carrier element 1, for example a semiconductor chip, the circuit 11 being connected to the detectors 2. Lines 20 connect the evaluation circuit 11 and the detectors 2.

The cavity 70 can be supplied from a liquid reservoir 71 with a liquid suitable for storing or washing the cell 6 or keeping it wet. For excitation of the cell 6, the excitation medium from the excitation source 21 is fed to this liquid, the supply of the excitation medium in the example being controllable by a valve 81 disposed in the inlet line 8. The valve 81 is controlled in the example by the integrated evaluation circuit 11.

The excitation medium is chosen for example such that it influences the metabolism of the cell 6, so that metabolic processes become visible because of the luminophores referred to above and are detected by the detectors 2. Preferably, multiple excitation sources 21 are present and deliver an excitation medium independently of each other so that the behavior of the cell 6 toward different excitation media can be investigated sequentially.

In order to carry away the chemical substances stimulating the cell 6 once the detection process is over, rinsing takes place for example with the liquid from the reservoir 71, whereby the medium flows out through the outlet 9, or the liquid is suctioned off. The liquid supply from this reservoir 71 is preferably also controlled by a valve 72 that is controlled by the evaluation circuit 11.

Figure 2:
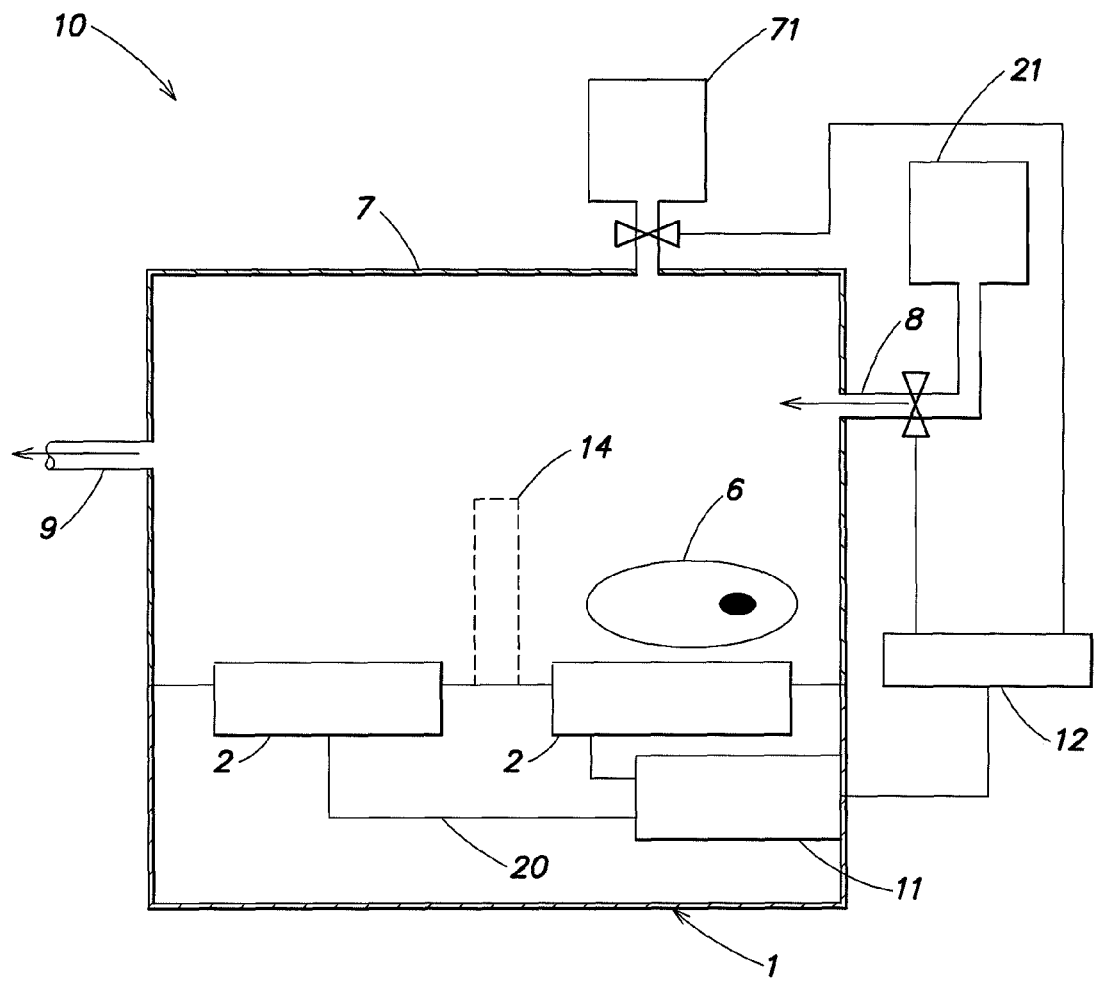
FIG. 2 is a side view in partial cross section of a second exemplary embodiment of a device according to the invention.

The valve 72 can also be controlled by an external control circuit 12 (FIG. 2), to which can be fed a signal from the evaluation circuit 11 dependent on the output signals of the detectors 2, as shown in FIG. 2.

FIG. 2 illustrates a second embodiment of a device 10 according to the invention in which two spatially separated detectors 2 are integrated into a carrier 1, for example a semiconductor body 1, below a surface suitable for receiving cells 6. Here, the cell 6 is immobilized above only one of the two detectors 2. The other detector 2 serves to prepare a reference value for the measured value delivered by the detector 2 below the cell 6. The reference value takes into account any luminescence signals unassociated with the excitation, resulting from natural florescence of the system components for example, and to be deducted from the measurement result. A partition 14 shown in dashed lines preferably projects upward from the carrier 1 to prevent the detector 2 that generates the reference value from being influenced by specific luminescence signals from the cell 6 or from the vicinity of the cell 6.

Figure 3:
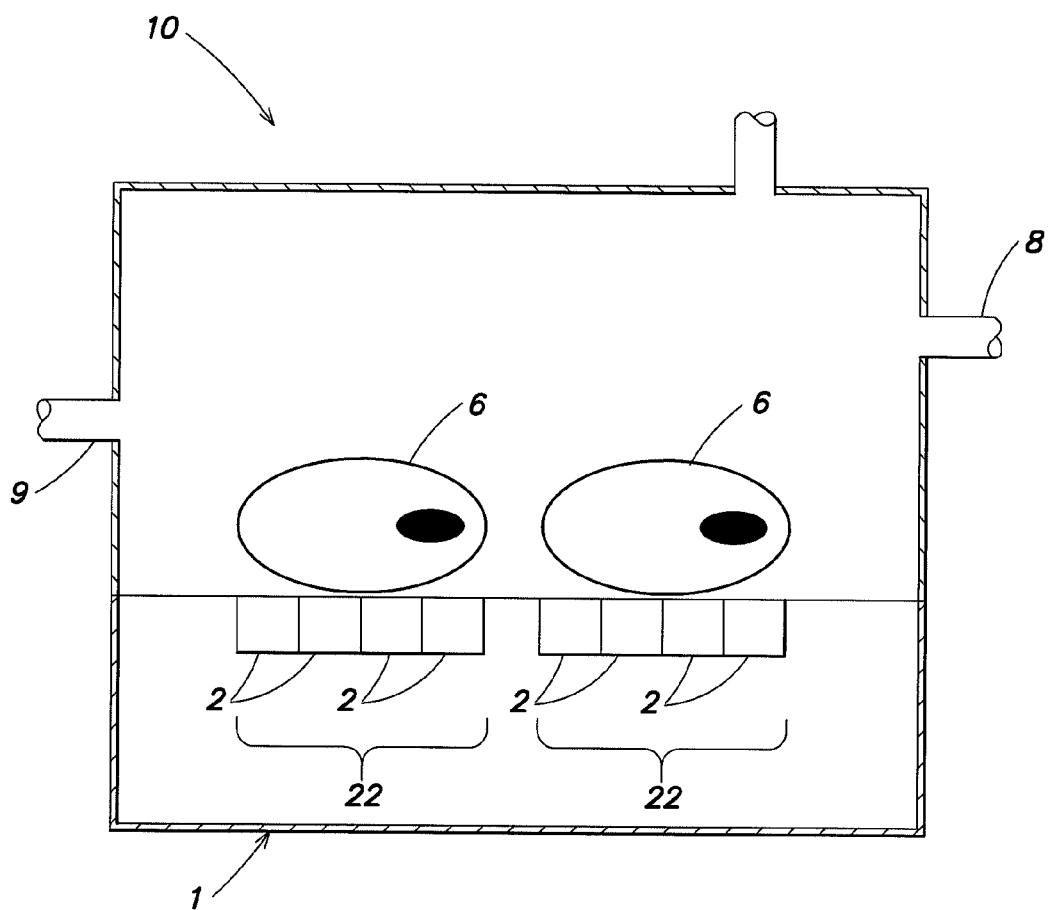
FIG. 3 is a side view in partial cross section of a third exemplary embodiment of a device according to the invention.

FIG. 3 illustrates another embodiment of a device 10 according to the invention with a carrier arrangement that differs from both of the previous embodiments of FIGS. 1-2 regarding the arrangement of the detectors 2. The embodiment in FIG. 3 does not show the excitation source 21 or the evaluation circuit 11, which are obviously present as well.

The carrier 1, preferably formed from a semiconductor chip, has two detector fields 22 in this example, each of which comprises a plurality of detectors 2. In this way, multiple measurements can be conducted at the same time, so that a statistical evaluation of the measurement signal specifically obtained can be derived. Thus it is possible for example to differentiate between nonspecific and specific signals, the specific signals being the signals resulting from metabolic processes in the cell 6 and the nonspecific signals being other signals, for example interference. These nonspecific signals have a different distribution from the specific signals, making differentiation possible.

Figure 4:
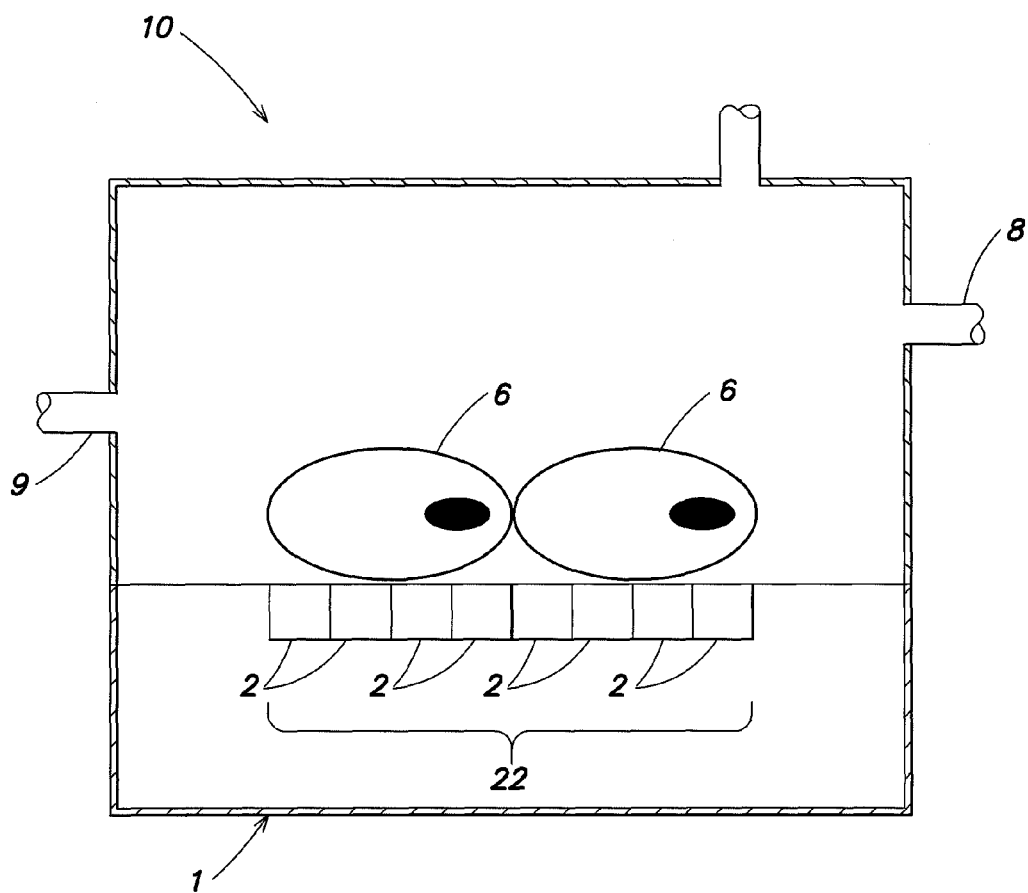
FIG. 4 is a side view in partial cross section of a fourth exemplary embodiment of a device according to the invention.

FIG. 4 illustrates a variant of a carrier element 1 shown in FIG. 3, which has one continuous detector field 22 with a plurality of detectors 2 suitable for examining multiple cells 6 simultaneously. This device 10 makes it possible to examine identical cells 6 under comparable conditions and detect their signals, and these signals obtained under identical conditions can be averaged in an evaluation circuit for a statistical check.

A method for manufacturing a carrier suitable for the device according to the invention will be explained briefly below:

A semiconductor chip is manufactured using six-inch wafers by a 0.5 micron CMOS process. The detectors 2 are disposed as pn-photodiodes in an n-well on a p-substrate. After field oxidation, the p-regions of the photodiode are defined and a 10 nm thick gate oxide layer is applied. If desired, a structured nitride (e.g. LPCVD or PECVD) can additionally be applied at this location as a UV filter. Next, a silicon dioxide layer is applied and structured. After this, the other normal CMOS steps are taken, such as application of a wiring layer and surface passivation (scratch protection).

The CMOS sensor so produced is modified by coating with a suitable cell growth substance such as gelatin. Individual cells (e.g. trypsinized epithelial cells) are seeded and allowed to grow in a cell culture medium (e.g. DMEM-F12).

The device 10 according to the invention is suitable for example for investigating the calcium metabolism of heart muscle cells 6. The cells 6 are first loaded with aequorin by osmotic shock treatment. Intracellular calcium signals in response to chemical stimuli by the chemical given off by excitation source 21 are made visible by the bioluminescence of the aequorin and detected by the detectors 2.

The device 10 according to the invention for investigating intracellular processes after biological or chemical excitation is particularly compact and can be made by known methods.

Although the present invention has been illustrated and described with respect to several preferred embodiments thereof, various changes, omissions and additions to the form and detail thereof, may be made therein, without departing from the spirit and scope of the invention.

What is claimed is:

1. A device for detecting a cellular metabolic process associated with a cell by detecting a luminescence event in, at, or in the immediate vicinity of the cell, the device comprising:
   a carrier element with a surface prepared for coupling of the cell thereto;
   a detector for receiving a luminescence signal indicative of the luminescent event through the prepared surface, where the detector is integrated into the carrier element below the prepared surface;
   a cover covering the prepared surface to form a cavity, the cover having an inlet and an outlet; and
   a metabolically-influencing cell excitation reservoir connected to the inlet and containing a biological or chemical excitation medium that includes a luminophore, where the excitation medium influences the metabolism of the cell during excitation thereof by the medium, and where the luminophore reacts with a metabolic product of the cell during the excitation thereof to thereby provide the luminescence signal.

2. The device of claim 1, further comprising an optical filter located between the prepared surface and the optical detector.

3. The device of claim 1, where the carrier element is a semiconductor body.

4. The device of claim 1, where a plurality of optical detectors are integrated into the carrier element below the prepared surface.

5. The device of claim 1, where the optical detector comprises a photodiode.

6. The device of claim 1, further comprising an evaluation circuit connected to the detector.

7. The device of claim 1, further comprising an evaluation circuit integrated into the carrier element.

8. The device of claim 1, further comprising an evaluation circuit that controls the excitation reservoir to send the chemical or biological excitation medium to the inlet opening.

9. The device of claim 1, further comprising a valve disposed in an inlet line between the excitation reservoir and the inlet to control a supply of the excitation medium to the inlet.

10. The device of claim 1, where the prepared surface includes an adhesion matrix and/or a growth substrate for the cell coupled thereto.

11. The device of claim 10, where the growth substrate comprises gelatin.

12. The device of claim 1, where the prepared surface has a cell-immobilizing medium applied thereto.

13. The device of claim 12, where the cell-immobilizing medium comprises negatively charged polystyrene.

14. The device of claim 1, where the cell is immobilized at the prepared surface.

15. The device of claim 1, where a depression is created in at least a portion of the prepared surface.

16. A device for detecting a cellular metabolic process associated with a cell by detecting a luminescence event in, at, or in the immediate vicinity of the cell, the device comprising:
   a semiconductive device with a surface prepared for coupling of the cell thereto;
   a detector for receiving a luminescence signal indicative of the luminescent event through the prepared surface, where the detector is integrated into the semiconductive device below the cell;
   a cover that covers the prepared surface to form a cavity, the cover having an inlet and an outlet; and
   a metabolically-influencing cell excitation reservoir that provides to the cavity via the inlet a biological or chemical excitation medium that includes a luminophore, where the excitation medium influences the metabolism of the cell during excitation thereof by the medium, and where the luminophore reacts with a metabolic product of the cell during the excitation thereof to provide luminescence detected by the detector.

17. The device of claim 16, further comprising an optical filter located between the prepared surface and the optical detector, and where a plurality of optical detectors are integrated into the semiconductive substrate below the prepared surface.

18. The device of claim 16, further comprising an evaluation circuit semiconductive that controls the excitation reservoir to send the chemical or biological excitation medium to the inlet opening.

19. The device of claim 16, where the prepared surface has a cell-immobilizing medium applied thereto.

20. A device for detecting a cellular metabolic process associated with a cell by detecting a luminescence event, the device comprising:
   a semiconductive device with a surface prepared with a cell-immobilizing medium for coupling and immobilizing of the cell thereto;
   a detector for receiving a luminescence signal indicative of the luminescent event through the prepared surface, where the detector is integrated into the semiconductive device below the cell and prepared surface;
   a housing that in cooperation with the prepared surface forms a cavity having an inlet and an outlet; and
   one of a metabolically-influencing cell excitation reservoir that provides to the cavity via the inlet a biological or chemical excitation medium that includes a luminophore, where the excitation medium influences the metabolism of the cell and the luminophore reacts with a metabolic product of the cell to provide luminescence detected by the detector.

* * * * *

UNITED STATES PATENT AND TRADEMARK OFFICE
CERTIFICATE OF CORRECTION

| | | |
|---|---|---|
| PATENT NO. | : 7,767,443 B2 | Page 1 of 1 |
| APPLICATION NO. | : 10/509040 | |
| DATED | : August 3, 2010 | |
| INVENTOR(S) | : Lehmann et al. | |

It is certified that error appears in the above-identified patent and that said Letters Patent is hereby corrected as shown below:

Column 9
Line 26, delete "forth" and insert --form--

Signed and Sealed this

Fourteenth Day of September, 2010

David J. Kappos
*Director of the United States Patent and Trademark Office*